United States Patent
Jautelat et al.

[11] Patent Number: 5,859,039
[45] Date of Patent: Jan. 12, 1999

[54] MICROBICIDAL TRIAZOLYL DERIVATIVES

[75] Inventors: Manfred Jautelat, Burscheid; Ralf Tiemann, Leverkusen; Stefan Dutzmann, Hilden; Gerd Hänssler, Leverkusen; Klaus Stenzel, Düsseldorf, all of Germany

[73] Assignee: Bayer Aktiengesellschaft, Leverkusen, Germany

[21] Appl. No.: 878,916

[22] Filed: Jun. 19, 1997

Related U.S. Application Data

[62] Division of Ser. No. 836,415, filed as PCT/EP95/04392, Nov. 8, 1995, Pat. No. 5,789,430.

[30] Foreign Application Priority Data

Nov. 21, 1994 [DE] Germany .......................... 44 41 354.8
Jul. 24, 1995 [DE] Germany ......................... 195 26 918.7
Jul. 31, 1995 [DE] Germany ......................... 195 28 046.6

[51] Int. Cl.$^6$ ...................... A01N 43/653; C07D 249/08
[52] U.S. Cl. ................... 514/384; 548/263.2; 548/264.4
[58] Field of Search ................ 514/384; 548/263.2, 548/264.4

[56] References Cited

U.S. PATENT DOCUMENTS

| | | |
|---|---|---|
| 4,913,727 | 4/1990 | Stroech et al. . |
| 4,952,232 | 8/1990 | Cuomo et al. ............ 71/92 |
| 5,288,883 | 2/1994 | Scherkenbeck et al. . |
| 5,462,955 | 10/1995 | Scherkenbeck et al. . |

*Primary Examiner*—Patricia L. Morris
*Attorney, Agent, or Firm*—Sprung Kramer Schaefer & Briscoe

[57] ABSTRACT

Triazolyl derivatives of the formula

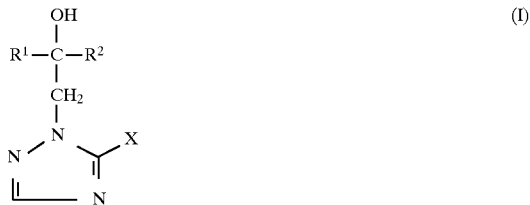

in which $R^1$ and $R^2$ are identical or different and represent optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl and X represents the groups —SH, —SR$^3$, —SO—R$^3$, —SO$_2$—R$^3$ or —SO$_3$H, in which $R^3$ represents alkyl which is optionally substituted by fluorine and/or chlorine, alkenyl which is optionally substituted by fluorine and/or chlorine, optionally substituted aralkyl or optionally substituted aryl, and their acid addition salts and metal salt complexes, a plurality of processes for the preparation of the new substances, and their use as microbicides in plant protection and materials protection.

4 Claims, No Drawings

MICROBICIDAL TRIAZOLYL DERIVATIVES

This is a division of application Ser. No. 08/836,415, filed on May 14, 1997 now U.S. Pat. No. 5,789,430, which is a 371 of PCT/EP95/04392, filed on Nov. 8, 1995.

The present invention relates to new triazolyl derivatives, to a plurality of processes for their preparation, and to their use as microbicides.

It has already been disclosed that a large number of hydroxyethyl-azolyl derivatives have fungicidal properties (cf. EP-A 0 015 756, EP-A 0 040 345, EP-A 0 052 424, EP-A 0 061 835 and EP-A 0 297 345). However, the applicability of these substances is not always satisfactory in some cases.

There have now been found new triazolyl derivatives of the formula

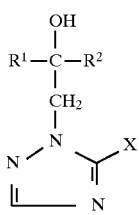
(I)

in which

R$^1$ and R$^2$ are identical or different and represent optionally substituted alkyl, optionally substituted alkenyl, optionally substituted cycloalkyl, optionally substituted aralkyl, optionally substituted aralkenyl, optionally substituted aroxyalkyl, optionally substituted aryl or optionally substituted heteroaryl and X represents the groups —SH, —SR$^3$, —SO—R$^3$, —SO—R$^3$ or —SO$_3$H, in which R$^3$ represents alkyl which is optionally substituted by fluorine and/or chlorine, alkenyl which is optionally substituted by fluorine and/or chlorine, optionally substituted aralkyl or optionally substituted aryl, and their acid addition salts and metal salt complexes.

Those substances according to the invention in which R$^1$ and R$^2$ are different have an asymmetrically substituted carbon atom. They can therefore be obtained in the form of optical isomers. The present invention relates to the individual isomers as well as their mixtures.

Furthermore, it has been found that triazolyl derivatives of the formula (I) and their acid addition salts and metal salt complexes are obtained when a) hydroxyethyl-triazoles of the formula

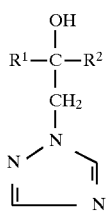
(II)

in which

R$^1$ and R$^2$ have the abovementioned meanings, either

α) are reacted in succession with strong bases and sulphur in the presence of a diluent and the product is then hydrolysed with water, if appropriate in the presence of an acid, or β) are reacted with sulphur in the presence of a high-boiling diluent and then treated, if appropriate, with water and, if appropriate, with acid, and if appropriate the compounds resulting according to variants (α) and (β), of the formula

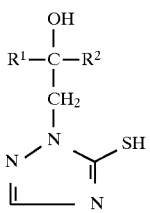
(Ia)

in which

R$^1$ and R$^2$ have the abovementioned meanings, are reacted with halogen compounds of the formula

R$^4$—Hal (III)

in which

R$^4$ represents alkyl which is optionally substituted by fluorine and/or chlorine, alkenyl which is optionally substituted by fluorine and/or chlorine or optionally substituted aralkyl and Hal represents chlorine, bromine or iodine, in the presence of an acid-binding agent and in the presence of a diluent and, if appropriate, the resulting compounds of the formula

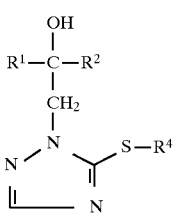
(Ib)

in which

R$^1$, R$^2$ and R$^4$ have the abovementioned meanings, are reacted with oxidants in the presence of a diluent, or b) hydroxyethyl-triazoles of the formula

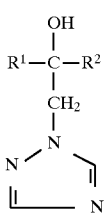
(II)

in which

R$^1$ and R$^2$ have the abovementioned meanings, are reacted in succession with strong bases and diaryl disulphides of the formula

R$^5$—S—S—R$^5$ (IV)

in which

R$^5$ represents optionally substituted aryl, in the presence of a diluent and, if appropriate, the resulting compounds of the formula

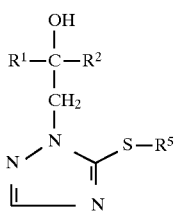

(Ic)

in which

R$^1$, R$^2$ and R$^5$ have the abovementioned meanings, are reacted with oxidants in the presence of a diluent, or c) triazolyl derivatives of the formula

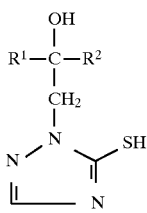

(Ia)

in which

R$^1$ and R$^2$ have the abovementioned meanings, are reacted with potassium permanganate in the presence of a diluent, and, if appropriate, the resulting compounds of the formula (I) are then subjected to an addition reaction with an acid or a metal salt.

Finally, it has been found that the new triazolyl derivatives of the formula (I) and their acid addition salts and metal salt complexes have very good microbicidal properties and can be used both in plant protection and in materials protection to control undesirable microorganisms, such as fungi.

Surprisingly, the substances according to the invention have a better microbicidal activity, in particular fungicidal activity than those compounds of the same direction of action which are most similar constitutionally.

Formula (I) provides a general definition of triazolyl derivatives according to the invention.

R$^1$ preferably represents straight-chain or branched alkyl having 1 to 6 carbon atoms, it being possible for these radicals to be monosubstituted to tetrasubstituted by identical or different substituents from the series consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, it being possible for each of these radicals to be monosubstituted to trisubstituted by identical or different substituents from the series consisting of halogen, alkoxy having 1 to 4 carbon atoms and/or cycloalkyl having 3 to 7 carbon atoms, or represents cycloalkyl having 3 to 7 carbon atoms, it being possible for each of these radicals to be monosubstituted to trisubstituted by identical or different substituents from the series consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, it being possible for the aryl moiety in each case to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, it being possible for the aryl moiety in each case to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, it being possible for the aryl moiety in each case to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aryl having 6 to 10 carbon atoms, it being possible for each of these radicals to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused five- or six-membered heteroaromatic radical having 1 to 3 heteroatoms, such as nitrogen, sulphur and/or oxygen, it being possible for each of these radicals to be monosubstituted to trisubstituted by identical or different substituents from the series consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano.

$R^2$ preferably represents straight-chain or branched alkyl having 1 to 6 carbon atoms, it being possible for these radicals to be monosubstituted to tetrasubstituted by identical or different substituents from the series consisting of halogen, alkoxy having 1 to 4 carbon atoms, alkoximino having 1 to 4 carbon atoms in the alkoxy moiety and/or cycloalkyl having 3 to 7 carbon atoms, or represents straight-chain or branched alkenyl having 2 to 6 carbon atoms, it being possible for each of these radicals to be monosubstituted to trisubstituted by identical or different substituents from the series consisting of halogen, alkoxy having 1 to 4 carbon atoms and/or cycloalkyl having 3 to 7 carbon atoms, or represents cycloalkyl having 3 to 7 carbon atoms, it being possible for each of these radicals to be monosubstituted to trisubstituted by identical or different substituents from the series consisting of halogen, cyano and/or alkyl having 1 to 4 carbon atoms, or represents aralkyl having 6 to 10 carbon atoms in the aryl moiety and 1 to 4 carbon atoms in the straight-chain or branched alkyl moiety, it being possible for the aryl moiety in each case to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aralkenyl having 6 to 10 carbon atoms in the aryl moiety and 2 to 4 carbon atoms in the alkenyl moiety, it being possible for the aryl moiety in each case to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents aroxyalkyl having 6 to 10 carbon atoms in the aryl moiety and 1 to 4 carbon atoms in the straight-chain or branched oxyalkyl moiety, it being possible for the aryl moiety in each case to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having, 1 to 4 carbon atoms in the alkoxy moiety and 1 to 4 carbon atoms in the alkyl moiety, nitro and/or cyano, or represents aryl having 6 to 10 carbon atoms, it being possible for each of these radicals to be monosubstituted to trisubstituted by identical or different substituents from the series consisting of halogen, alkyl having 1 to 4 carbon atoms, alkoxy having 1 to 4 carbon atoms, alkylthio having 1 to 4 carbon atoms, halogenoalkyl having 1 or 2 carbon atoms and 1 to 5 identical or different halogen atoms, halogenoalkoxy having 1 or 2 carbon atoms and 1 to 5 identical or different halogen atoms, halogenoalkylthio having 1 or 2 carbon atoms and 1 to 5 identical or different halogen atoms, cycloalkyl having 3 to 7 carbon atoms, phenyl, phenoxy, alkoxycarbonyl having 1 to 4 carbon atoms in the alkoxy moiety, alkoximinoalkyl having 1 to 4 carbon atoms in the alkoxy moiety and 1 to 4 carbon atoms in the alkyl moiety, nitro and/or cyano, or represents an optionally benzo-fused five- or six-membered heteroaromatic radical having 1 to 3 heteroatoms, such as nitrogen, sulphur and/or oxygen, it being possible for each of these radicals to be monosubstituted to trisubstituted by identical or different substituents from the series consisting of halogen, alkyl having 1 to 4 carbon atoms, hydroxyalkyl having 1 to 4 carbon atoms, hydroxyalkinyl having 3 to 8 carbon atoms, alkoxy having 1 or 2 carbon atoms, alkylthio having 1 or 2 carbon atoms, halogenoalkyl, halogenoalkoxy and halogenoalkylthio, each of which has 1 or 2 carbon atoms and 1 to 5 identical or different halogen atoms, such as fluorine or chlorine atoms, formyl, dialkoxymethyl having 1 or 2 carbon atoms in each alkoxy group, acyl having 2 to 4 carbon atoms, alkoxycarbonyl having 1 to 4 carbon atoms in the alkoxy moiety, alkoximinoalkyl having 1 to 4 carbon atoms in the alkoxy moiety and 1 to 3 carbon atoms in the alkyl moiety, nitro and/or cyano.

X also preferably represents the groups —SH, —SR$^3$, —SO—R$^3$, —SO$_2$—R$^3$ or —SO$_3$H.

R$^3$ preferably represents straight-chain or branched alkyl having 1 to 6 carbon atoms, it being possible for each of these radicals to be monosubstituted to trisubstituted by fluorine and/or chlorine, or represents straight-chain or branched alkenyl having 2 to 6 carbon atoms, it being possible for each of these radicals to be monosubstituted to trisubstituted by fluorine and/or chlorine, or represents phenylalkyl having 1 to 4 carbon atoms in the straight-chain or branched alkyl moiety, it being possible for each of these radicals to be monosubstituted to trisubstituted in the phenyl moiety by identical or different substituents from the series consisting of halogen, alkyl having 1 to 4 carbon atoms, and/or halogenoalkyl having 1 to 4 carbon atoms and 1 to 5 halogen atoms, or represents phenyl which can be monosubstituted to trisubstituted by identical or different substituents from the series consisting of halogen, alkyl having 1 to 4 carbon atoms, and/or halogenoalkyl having 1 to 4 carbon atoms and 1 to 5 halogen atoms.

R$^1$ particularly preferably represents straight-chain or branched alkyl having 1 to 4 carbon atoms, it being possible for these radicals to be monosubstituted to tetrasubstituted by identical or different substituents from the series consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, it being possible for each of these radicals to be monosubstituted to trisubstituted by identical or different substituents from the series consisting of fluorine, chlorine, bromine, methoxy, ethoxy, propoxy, isopropoxy, cyclopropyl, cyclobutyl, cyclopentyl and/or cyclohexyl, or represents cycloalkyl having 3 to 6 carbon atoms, it being possible for each of these radicals to be monosubstituted to trisubstituted by identical or different substituents from the series consisting of fluorine, chlorine, bromine, cyano, methyl, ethyl, propyl, ispropyl and/or tert-butyl, or represents phenylalkyl having 1 to 4 carbon atoms in the straight-chain or branched alkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenylalkenyl having 2 to 4 carbon atoms in the alkenyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximino-methyl, 1-methoximinoethyl, nitro and/or cyano, or represents phenoxyalkyl having, 1 to 4 carbon atoms in the straight-chain or branched oxyalkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximino-methyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl nitro and/or cyano, formyl, dimethoxymethyl, acetyl and/or propionyl.

R$^2$ particularly preferably represents straight-chain or branched alkyl having 1 to 4 carbon atoms, it being possible for these radicals to be monosubstituted to tetrasubstituted by identical or different substituents from the series consisting of fluorine, chlorine, bromine, methoxy, ethoxy, propoxy, isopropoxy, alkoximino having 1 or 2 carbon atoms in the alkoxy moiety, cyclopropyl, cyclobutyl, cyclopentyl and/or cyclohexyl, or represents straight-chain or branched alkenyl having 2 to 5 carbon atoms, it being possible for each of these radicals to be monosubstituted to trisubstituted by identical or different substituents from the series consisting of fluorine, chlorine, bromine, methoxy, ethoxy, propoxy, isopropoxy, cyclopropyl, cyclobutyl, cyclopentyl and/or cyclohexyl, or represents cycloalkyl having 3 to 6 carbon atoms, it being possible for each of these radicals to be monosubstituted to trisubstituted by identical or different substituents from the series consisting of fluorine, chlorine, bromine, cyano, methyl, ethyl, propyl, isopropyl and/or tert-butyl, or represents phenylalkyl having 1 to 4 carbon atoms in the straight-chain or branched alkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenylalkenyl having 2 to 4 carbon atoms in the alkenyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenoxyalkyl having 1 to 4 carbon atoms in the straight-chain or branched oxyalkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl nitro and/or cyano, or represents phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl.

X also particularly preferably represents the groups —SH, —SR$^3$, —SO—R$^3$, —SO$_2$—R$^3$ or —SO$_3$H.

R$^3$ particularly preferably represents straight-chain or branched alkyl having 1 to 4 carbon atoms, it being possible for each of these radicals to be monosubstituted to trisubstituted by fluorine and/or chlorine, or represents straight-chain or branched alkenyl having, 2 to 5 carbon atoms, it being possible for each of these radicals to be monosubstituted to trisubstituted by identical or different substituents from the series consisting of fluorine and/or chlorine, or represents phenylalkyl having 1 to 3 carbon atoms in the straight-chain or branched alkyl moiety, it being possible for each of these radicals to be monosubstituted to trisubstituted in the phenyl moiety by identical or different substituents from the series consisting of fluorine, chlorine, bromine, methyl, ethyl, tert-butyl, trichloromethyl and/or trifluoromethyl, or represents phenyl which can be monosubstituted to trisubstituted by identical or different substituents from the series consisting of fluorine, chlorine, bromine, methyl, ethyl, tert-butyl, trichloromethyl.

R$^1$ very particularly preferably represents n-propyl, isopropyl, n-butyl, i-butyl, sec-butyl or tert-butyl, it being possible for these radicals to be monosubstituted to tetrasubstituted by identical or different substituents from the series consisting of fluorine, chlorine, bromine, methoxy, ethoxy, propoxy, isopropoxy, methoximino, ethoximino, cyclopropyl, cyclobutyl, cyclopentyl and/or cyclohexyl, or represents straight-chain or branched alkenyl having 2 to 5 carbon atoms, it being possible for each of these radicals to be monosubstituted to trisubstituted by identical or different substituents from the series consisting of fluorine, chlorine, bromine, methoxy, ethoxy, propoxy, isopropoxy, cyclopropyl, cyclobutyl, cyclopentyl and/or cyclohexyl, or represents 1-methyl-cyclohexyl, cyclohexyl, 1-chlorocyclopropyl, 1-fluorocyclopropyl, 1-methylcyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoxyiminoethyl, nitro and/or cyano, or represents phenylalkenyl having 2 to 4 carbon atoms in the alkenyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents phenoxyalkyl having 1 to 4 carbon atoms in the straight-chain or branched oxyalkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoxyiminoethyl, nitro and/or cyano, or represents phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy chlorodifluoromethylthio, methoxycarbonyl, ethoxycarbonyl, methoximino-methyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl.

$R^2$ very particularly preferably represents n-propyl, isopropyl, n-butyl, i-butyl, sec-butyl or tert-butyl, it being possible for these radicals to be monosubstituted to tetrasubstituted by identical or different substituents from the series consisting of fluorine, chlorine, bromine, methoxy, ethoxy, propoxy, isopropoxy, methoximino, ethoximino, cyclopropyl, cyclobutyl, cyclopentyl and/or cyclohexyl, or represents straight-chain or branched alkenyl having 2 to 5 carbon atoms, it being possible for each of these radicals to be monosubstituted to trisubstituted by identical or different substituents from the series consisting of fluorine, chlorine, bromine, methoxy, ethoxy, propoxy, isopropoxy, cyclopropyl, cyclobutyl, cyclopentyl and/or cyclohexyl, or represents 1-methyl-cyclohexyl, cyclohexyl, 1-chlorocyclopropyl, 1-fluorocyclopropyl, 1-methyl-cyclopropyl, 1-cyano-cyclopropyl, cyclopropyl, 1-methyl-cyclopentyl or 1-ethyl-cyclopentyl, or represents phenylalkyl having 1 or 2 carbon atoms in the straight-chain or branched alkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinioethyl, nitro and/or cyano, or represents phenylalkenyl having 2 to 4 carbon atoms in the alkenyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximino-methyl, 1-methoximinoethyl, nitro and/or cyano, or represents phenoxyalkyl having 1 to 4 carbon atoms in the straight-chain or branched oxyalkyl moiety, it being possible for the phenyl moiety to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoxyiminoethyl, nitro and/or cyano, or represents phenyl which can be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and/or cyano, or represents pyrazolyl, imidazolyl, 1,2,4-triazolyl, pyrrolyl, furanyl, thienyl, thiazolyl, oxazolyl, pyridinyl, pyrimidinyl, triazinyl, quinolinyl, isoquinolinyl, quinazolinyl, indolyl, benzothienyl, benzofuranyl, benzothiazolyl or benzimidazolyl, it being possible for each of these radicals to be monosubstituted to trisubstituted by identical or different substituents from the series consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, chlorodifluoromethylthio, hydroxymethyl, hydroxyethyl, hydroxyalkinyl having 4 to 6 carbon atoms, methoxycarbonyl, ethoxycarbonyl, methoximinomethyl, 1-methoximinoethyl, nitro and/or cyano, formyl, dimethoxymethyl, acetyl and/or propionyl.

X also very particularly preferably represents the groups —SH, —$SR^3$, —SO—$R^3$, —$SO_2$—$R^3$ or —$SO_3H$.

R³ very particularly preferably represents methyl, ethyl or propyl, it being possible for each of these radicals to be monosubstituted to trisubstituted by identical or different substituents from the series consisting of fluorine and/or chlorine, or represents allyl, but-2-en-yl or but-3-enyl, it being possible for each of these radicals to be monosubstituted to trisubstituted by identical or different substituents from the series consisting of fluorine and/or chlorine, or represents phenylalkyl having 1 or 2 carbon atoms in the straight-chain or branched alkyl moiety, it being possible for each of these radicals to be monosubstituted or disubstituted in the phenyl moiety by fluorine, chlorine, bromine, methyl, ethyl, tert-butyl, trichloromethyl and/or trifluoromethyl, or represents phenyl which can be monosubstituted or disubstituted by fluorine, chlorine, bromine, methyl, ethyl, tert-butyl, trichloromethyl and/or trifluoromethyl.

Other preferred compounds according to the invention are adducts of acids and those triazolyl derivatives of formula (I), in which $R^1$, $R^2$ and X have those meanings which have been mentioned as being preferred for these substituents.

The acids which can be subjected to an addition reaction preferably include hydrohalic acids, such as, for example, hydrochloric acid and hydrobromic acid, in particular hydrochloric acid, furthermore phosphoric acid, nitric acid, mono- and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and also sulphonic acids, such as, for example, p-toluenesulphonic acid and 1,5-naphthalenedisulphonic acid as well as saccharin and thiosaccharin.

Other preferred compounds according to the invention are adducts of salts of metals of main groups II to IV and sub-groups I and II and IV to VIII of the Periodic Table of the Elements and those triazolyl derivatives of the formula (I), in which $R^1$, $R^2$ and X have those meanings which have been mentioned as being preferred for these substituents.

Salts of copper, zinc, manganese, magnesium, tin, iron and nickel are particularly preferred in this context. Suitable anions of these salts are those which are derived from acids which lead to physiologically acceptable adducts. Particularly preferred acids of this type are, in this context, the hydrohalic acids, such as, for example, hydrochloric acid and hydrobromic acid, furthermore phosphoric acid, nitric acid and sulphuric acid.

The triazolyl derivatives of the formula (I) according to the invention, in which X represents an —SH group, can be present in the "mercapto" form of the formula $$R^1-\underset{\underset{CH_2}{|}}{\overset{\overset{OH}{|}}{C}}-R^2 \quad \text{(Ia)}$$

(with triazole-SH ring)

or in the tautomeric "thiono" form of the formula $$R^1-\underset{\underset{CH_2}{|}}{\overset{\overset{OH}{|}}{C}}-R^2 \quad \text{(Id)}$$

(with triazole=S, NH ring)

For the sake of simplicity, only the "mercapto" form is shown in each case.

Examples of substances according to the invention which may be mentioned are the triazolyl derivatives listed in the table which follows.

TABLE 1

$$R^1-\underset{\underset{CH_2}{|}}{\overset{\overset{OH}{|}}{C}}-R^2 \quad \text{(I)}$$

(with triazole-X ring)

| R¹ | R² | X |
|---|---|---|
| Cl—⟨C₆H₄⟩—CH₂—CH₂— | —C(CH₃)₃ | —SH |
| Cl—⟨C₆H₄⟩—CH₂—CH₂— | —C(CH₃)₃ | —SCH₃ |
| Cl—⟨C₆H₄⟩—CH₂—CH₂— | —C(CH₃)₃ | —SO—CH₃ |

TABLE 1-continued

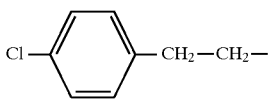

| R¹ | R² | X |
|---|---|---|
| Cl—⟨benzene⟩—CH₂—CH₂— | —C(CH₃)₃ | —SO₂—CH₃ |
| Cl—⟨benzene⟩—CH₂—CH₂— | —C(CH₃)₃ | —S—CH₂—⟨benzene⟩ |
| Cl—⟨benzene⟩—CH₂—CH₂— | —C(CH₃)₃ | —SO₃H |
| Cl—⟨benzene⟩—CH₂—CH₂— | —C(CH₃)₃ | —S—CH₂—CH=CH₂ |
| Cl—⟨benzene⟩—CH₂— | —C(CH₃)₃ | —SH |
| Cl—⟨benzene⟩—CH₂— | —C(CH₃)₃ | —SCH₃ |
| Cl—⟨benzene⟩—CH₂— | —C(CH₃)₃ | —SO—CH₃ |
| Cl—⟨benzene⟩—CH₂— | —C(CH₃)₃ | —SO₂—CH₃ |
| Cl—⟨benzene⟩—CH₂— | —C(CH₃)₃ | —S—CH₂—⟨benzene⟩ |
| Cl—⟨benzene⟩—CH₂— | —C(CH₃)₃ | —S—CH₂—CH=CH₂ |
| Cl—⟨benzene⟩—CH(CH₃)— | —C(CH₃)₃ | —SH |
| Cl—⟨benzene⟩—CH(CH₃)— | —C(CH₃)₃ | —SCH₃ |

TABLE 1-continued
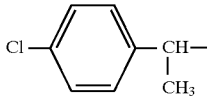
(I)
| R¹ | R² | X |
|---|---|---|
| 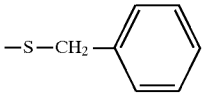 | $-C(CH_3)_3$ | 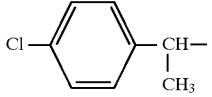 |
| 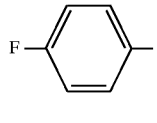 | $-C(CH_3)_3$ | $-S-CH_2-CH=CH_2$ |
| 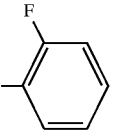 | 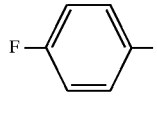 | $-SH$ |
| 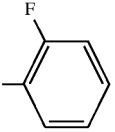 | 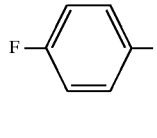 | $-SCH_3$ |
| 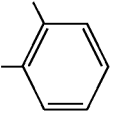 | 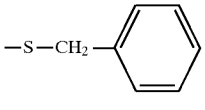 | 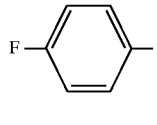 |
| 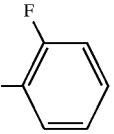 | 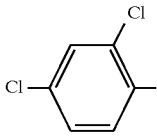 | $-S-CH_2-CH=CH_2$ |
| 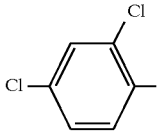 | $-C_4H_9\text{-}n$ | $-SH$ |
| 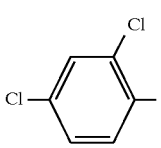 | $-C_4H_9\text{-}n$ | $-SCH_3$ |
| 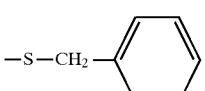 | $-C_4H_9\text{-}n$ | 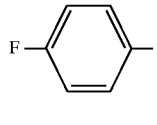 |

TABLE 1-continued $$\begin{array}{c} \text{OH} \\ | \\ R^1-C-R^2 \\ | \\ CH_2 \\ | \\ N\diagdown N \diagdown X \\ \| \quad \| \\ N \end{array} \quad (I)$$

| R¹ | R² | X |
|---|---|---|
| 2,4-dichlorophenyl | $-C_4H_9\text{-}n$ | $-S-CH_2-CH=CH_2$ |
| 4-chlorophenyl | $-CH(CH_3)\text{-cyclopropyl}$ | $-SH$ |
| 4-chlorophenyl | $-CH(CH_3)\text{-cyclopropyl}$ | $-SCH_3$ |
| 4-chlorophenyl | $-CH(CH_3)\text{-cyclopropyl}$ | $-S-CH_2-C_6H_5$ |
| 4-chlorophenyl | $-CH(CH_3)\text{-cyclopropyl}$ | $-S-CH_2-CH=CH_2$ |
| 4-chlorophenoxymethyl | $-C(CH_3)_3$ | $-SH$ |
| 4-chlorophenoxymethyl | $-C(CH_3)_3$ | $-SCH_3$ |
| 4-chlorophenoxymethyl | $-C(CH_3)_3$ | $-S-CH_2-C_6H_5$ |
| 4-chlorophenoxymethyl | $-C(CH_3)_3$ | $-S-CH_2-CH=CH_2$ |
| $Cl_2CH-CCl_2-CH_2-$ | $-C(CH_3)_3$ | $-SH$ |
| $Cl_2CH-CCl_2-CH_2-$ | $-C(CH_3)_3$ | $-SCH_3$ |
| $Cl_2CH-CCl_2-CH_2-$ | chlorocyclopropyl | $-SH$ |
| $Cl_2CH-CCl_2-CH_2-$ | chlorocyclopropyl | $-SCH_3$ |
| $Cl_2CH-CCl_2-CH_2-$ | fluorocyclopropyl | $-SH$ |

TABLE 1-continued (I)

$$\begin{array}{c} \text{OH} \\ | \\ R^1-C-R^2 \\ | \\ CH_2 \\ | \\ N-N \\ \| \quad \| \\ \quad \quad X \\ \quad \quad N \end{array}$$

| R¹ | R² | X |
|---|---|---|
| Cl₂CH—CCl₂—CH₂— | cyclopropyl-F | —SCH₃ |
| 4-Cl-C₆H₄—CH=CH— | —C(CH₃)₃ | —SH |
| 4-Cl-C₆H₄—CH=CH— | —C(CH₃)₃ | —SCH₃ |
| 4-Cl-C₆H₄—CH=CH— | cyclopropyl-Cl | —SCH₃ |
| 4-Cl-C₆H₄—CH₂—CH₂— | cyclopropyl-Cl | —SCH₃ |
| 4-Cl-C₆H₄—CH₂— | cyclopropyl-Cl | —SCH₃ |
| 4-Cl-C₆H₄—CH(CH₃)— | cyclopropyl-Cl | —SCH₃ |
| 4-Cl-C₆H₄—O—CH₂— | cyclopropyl-Cl | —SCH₃ |
| Cl₂CH—CCl₂— | cyclopropyl-Cl | —SCH₃ |
| 2-furyl-CH₂—CH₂— | —C(CH₃)₃ | —SCH₃ |
| 2-pyridyl-CH₂—CH₂— | —C(CH₃)₃ | —SCH₃ |
| 4-Cl-C₆H₄—CH₂—CH₂— | —C(CH₃)₃ | —S—C₆H₅ |

If 2-(1-chloro-cyclopropyl)-1-(2-chlorophenyl)-3-(1,2,4-triazol-1-yl)-propan-2-ol is used as starting substance, n-butyl-lithium as strong base and sulphur powder as reactant, the course of the first step of process (a), variant (a), according to the invention can be illustrated by the following equation:

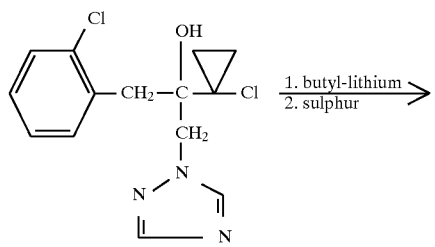

If 2-(1-chloro-cyclopropyl)-1-(2-chloro-phenyl)-3-(1,2,4-triazol-1-yl)-propan-2-ol is used as starting substance, sulphur powder as reactant and N-methyl-pyrrolidone as diluent, the course of the first step of process (a), variant (β), according to the invention can be illustrated by the following equation:

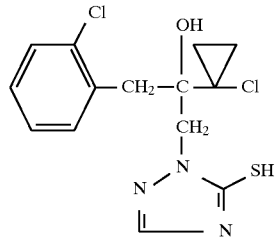

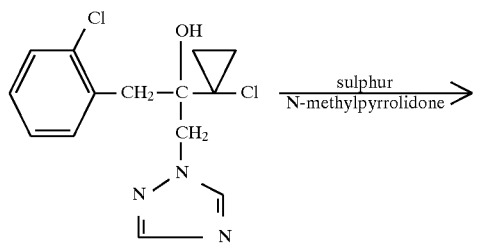

If 2-(1-chloro-cyclopropyl)-1-(2-chlorophenyl)-3-(5-mercapto-1,2,4-triazol-1-yl)-propan-2-ol is used as starting substance and methyl iodide as a reactant, the course of the second step of process (a) according to the invention can be illustrated by the following equation:

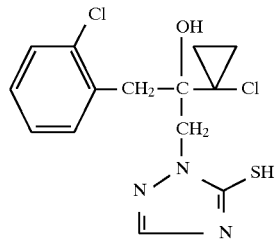

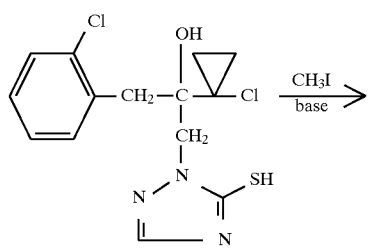

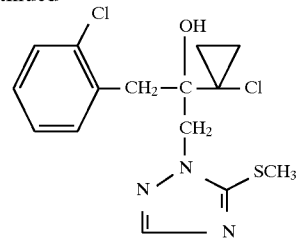

If 2-(1-chloro-cyclopropyl)-1-(2-chlorophenyl)-3-(5-methylthio-1,2,4-triazol-1-yl)-propan-2-ol is used as starting substance and an excess of hydrogen peroxide as oxidant, the course of the third step of process (a) according to the invention can be illustrated by the following equation:

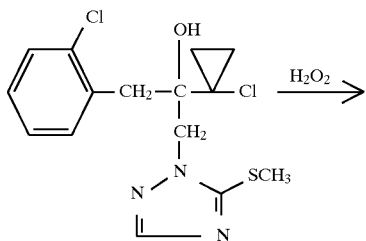

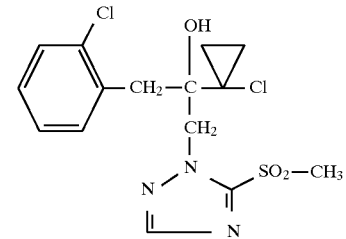

If 2-(1-chloro-cyclopropyl)-1-(2-chlorophenyl)-3-(1,2,4-triazol-1-yl)-propan-2-ol is used as starting substance, n-butyl-lithium as strong base and diphenyl disulphide as reactant, the course of the first step of process (b) according to the invention can be illustrated by the following equation:

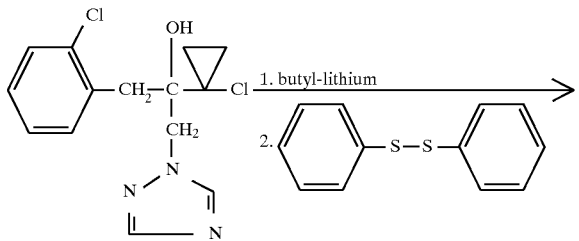

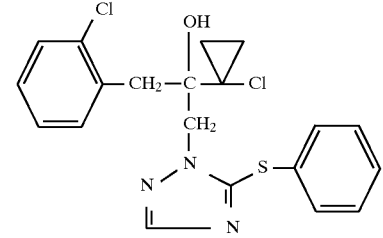

If 2-(1-chloro-cyclopropyl)-1-(2-chlorophenyl)-3-(5-phenylthio-1,2,4-triazol-1-yl)-propan-2-ol is used and reacted with an equimolar amount of hydrogen peroxide as oxidant, the course of the second step of process (b) according to the invention can be illustrated by the following equation:

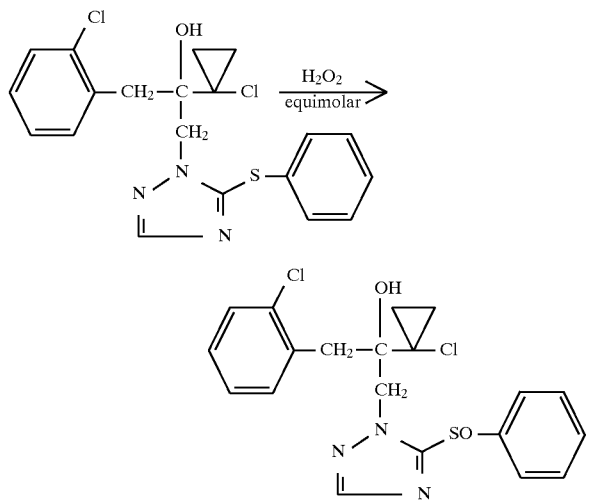

If 2-(1-chloro-cyclopropyl)- -(2-chlorophenyl)-3-(5-mercapto-1,2,4-triazol-1-yl)-propan-2-ol is used as starting substance and potassium permanganate as oxidant, the course of process (c) according to the invention can be illustrated by the following equation:

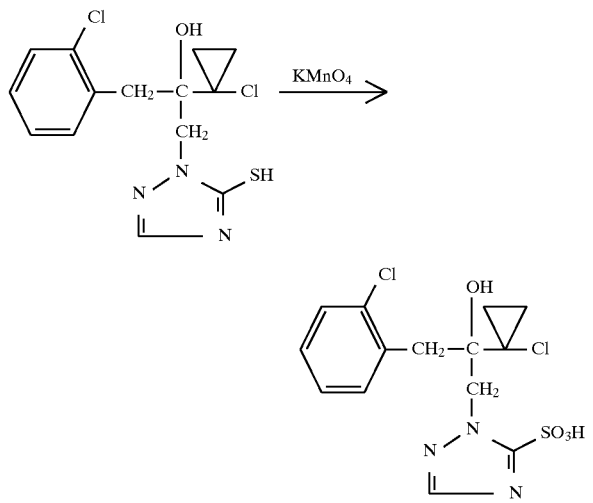

Formula (II) provides a general definition of the hydroxyethyl-triazoles required as starting substances for carrying out process (a) according to the invention. In this formula, $R^1$ and $R^2$ preferably have those meanings which have already been mentioned in connection with the description of the substances of the formula (I) according to the invention as being preferred for these radicals.

The hydroxyethyl-triazoles of the formula (II) are known or can be prepared by known methods (cf. EP-A 0 015 756, EP-A 0 040 345, EP-A 0 052 424, EP-A 0 061 835, EP-A 0 297 345 and EP-A 0 470 463).

Suitable bases for carrying out the first step of process (a), variant (α), according to the invention are all strong alkali metal bases which are customary for such reactions. The following can preferably be used: n-butyl-lithium, lithium diisopropylamide, sodium hydride, sodium amide and also potassium tert-butylate as a mixture with tetramethylethylene-diamine (=TMEDA).

When carrying out the first step of process (a), variant (α), according to the invention, suitable diluents are all inert organic solvents which are customary for such reactions. The following can preferably be used: ethers, such as tetrahydrofuran, dioxane, diethyl ether and 1,2-dimethoxyethane, furthermore liquid ammonia or else strongly polar solvents, such as dimethyl sulphoxide.

Sulphur is preferably employed in the form of a powder. For the hydrolysis when carrying out the first step of process (a), variant (α), according to the invention, water is used, if appropriate in the presence of an acid. Suitable acids are all inorganic or organic acids which are customary for such reactions. Acetic acid, dilute sulphuric acid and dilute hydrochloric acid can preferably be used. However, the hydrolysis can also be carried out using aqueous ammonium chloride solution.

When carrying out the first step of process (a), variant (α), according to the invention, the reaction temperatures can be varied within a certain range. In general, the process is carried out at temperatures between -70° C. and +20° C., preferably between -70° C. and 0° C.

All steps of process (a) according to the invention are generally carried out under atmospheric pressure. However, it is also possible to work at elevated or reduced pressure. Especially when carrying out the first step of process (a) according to the invention according to variant (α), working, at increased pressure is suitable.

When carrying out the first step of process (a) according to the invention according to variant (α), 2 to 3 equivalents, preferably 2.0 to 2.5 equivalents, of strong base and subsequently an equivalent amount or else an excess of sulphur are generally employed relative to 1 mol of hydroxyethyl-triazole of the formula (II). The reaction can be carried out under protective gas atmosphere, for example under nitrogen or argon. Working-up is carried out by customary methods. In general, a procedure is followed in which the reaction mixture is extracted using an organic solvent which is sparingly soluble in water, the combined organic phases are dried and concentrated, and, if desired, the residue which remains is purified by recrystallization and/or chromatography.

When carrying out the first step of process (a) according to the invention according to variant (β), suitable diluents are all high-boiling organic solvents which are customary for reactions of this type. Amides, such as dimethylformamide and dimethylacetamide, can be preferably used, and additionally heterocyclic compounds, such as N-methylpyrrolidone, and also ethers, such as diphenyl ether.

Sulphur is also in general employed in the form of powder when carrying out the first step of process (a) according to the invention according to variant (β). After the reaction, if appropriate, a treatment with water and, if appropriate, with acid can be carried out. This is carried out like the hydrolysis when carrying out the first step of process (a) according to the invention according to variant (α).

The reaction temperatures can also be varied within a relatively wide range when carrying out the first step of process (a) according to the invention according to variant (β). In general, the reaction is carried out at temperatures between 150° C. and 300° C., preferably between 180° C. and 250° C.

When carrying out the first step of process (a) according to the invention according to variant (β), in general 1 to 5 mol, preferably 1.5 to 3 mol, of sulphur are employed relative to 1 mol of hydroxyethyl-triazole of the formula (II). Working-up is carried out by customary methods. In general, a procedure is followed in which the reaction mixture is extracted using an organic solvent which is only sparingly soluble in water, the combined organic phases are dried and concentrated and the residue which remains is optionally freed from impurities which are possibly present according to customary methods, such as recrystallization or chromatography.

The compounds of the formula (Ia) which are required as starting substances for carrying out the second step of process (a) according to the invention are substances according to the invention.

Formula (III) provides a general definition of the halogen compounds required as reactants for carrying out the second step of process (a) according to the invention.

$R^4$ preferably represents straight-chain or branched alkyl having 1 to 6 carbon atoms, it being possible for each of these radicals to be monosubstituted to trisubstituted by fluorine and/or chlorine, or represents straight-chain or branched alkenyl having 2 to 6 carbon atoms, it being possible for each of these radicals to be monosubstituted to trisubstituted by fluorine and/or chlorine, or represents phenylalkyl having 1 to 4 carbon atoms in the straight-chain or branched alkyl moiety, it being possible for each of these radicals to be monosubstituted to trisubstituted in the phenyl moiety by identical or different substituents from the series consisting of halogen, alkyl having 1 to 4 carbon atoms and/or halogenoalkyl having 1 to 4 carbon atoms and 1 to 5 halogen atoms.

$R^4$ particularly preferably represents straight-chain or branched alkyl having 1 to 4 carbon atoms, it being possible for each of these radicals to be monosubstituted to trisubstituted by fluorine and/or chlorine, or represents straight-chain or branched alkenyl having 2 to 5 carbon atoms, it being possible for each of these radicals to be monosubstituted to trisubstituted by identical or different substituents from the series consisting of fluorine and/or chlorine, or represents phenylalkyl having 1 to 3 carbon atoms in the straight-chain or branched alkyl moiety, it being possible for each of these radicals to be monosubstituted to trisubstituted in the phenyl moiety by identical or different substituents from the series consisting of fluorine, chlorine, bromine, methyl, ethyl, tert-butyl, trichloromethyl and/or trifluoromethyl.

$R^4$ very particularly preferably represents methyl, ethyl or propyl, it being possible for each of these radicals to be monosubstituted to trisubstituted by identical or different substituents from the series consisting of fluorine and chlorine, or represents allyl, but-2-en-yl or but-3-enyl, it being possible for each of these radicals to be monosubstituted to trisubstituted by identical or different substituents from the series consisting of fluorine and/or chlorine, or represents phenylalkyl having 1 to 2 carbon atoms in the straight-chain or branched alkyl moiety, it being possible for each of these radicals to be monosubstituted or disubstituted in the phenyl moiety by fluorine, chlorine, bromine, methyl, ethyl, tert-butyl, trichloromethyl and/or trifluoromethyl.

Hal also preferably represents chlorine, bromine or iodine.

The halogen compounds of the formula (III) are known.

Suitable acid-binding agents for carrying out the second step of process (a) according to the invention are all customary inorganic or organic bases. The following can preferably be used: alkaline earth metal hydroxides or alkali metal hydroxides, such as sodium hydroxide, calcium hydroxide, potassium hydroxide, or else ammonium hydroxide, alkali metal carbonates, such as sodium carbonate, potassium carbonate, potassium hydrogen carbonate, sodium hydrogen carbonate, alkali metal acetates or alkaline earth metal acetates, such as sodium acetate, potassium acetate, calcium acetate, and also tertiary amines, such as trimethylamine, triethylamine, tributylamine, N,N-dimethylaniline, pyridine, N-methyl-piperidine, N,N-dimethylaminopyridine, diazabicyclooctane (DABCO), diazabicyclonone (DBN) or diazabicycloundecene (DBU).

Suitable diluents for carrying out the second step of the process (a) according to the invention are all inert organic solvents which are customary for such reactions. The following can preferably be used: ethers, such as diethyl ether, methyl tert-butyl ether, ethylene glycol dimethyl ether, tetrahydrofuran and dioxane, furthermore nitriles, such as acetonitrile, and additionally strong polar solvents, such as dimethyl sulphoxide or dimethylformamide.

When carrying out the second step of process (a) according to the invention, the reaction temperatures can be varied within a relatively wide range. In general, the process is carried out at temperatures between 0° C. and 120° C., preferably between 20° C. and 100° C.

When carrying out the second step of process (a) according to the invention, 1 to 2 mol of halogen compound of the formula (III) and an equivalent amount or else an excess of acid-binding agent are generally employed relative to 1 mol of triazolyl derivative of the formula (Ia). Working-up is carried out by customary methods. In general, a procedure is followed in which the reaction mixture is treated with aqueous base and an organic solvent which is sparingly miscible with water, and the organic phase is separated off, dried and concentrated. If appropriate, the product obtained can be freed from any impurities still present by customary methods, for example by recrystallization.

The compounds of the formula (Ib) which are required as starting substances for carrying out the third step of process (a) according to the invention are substances according to the invention.

Suitable oxidants for carrying out the third step of process (a) according to the invention are all substances conventionally used for the oxidation of sulphur. The following can preferably be used: hydrogen peroxide and peracids, such as peracetic acid and meta-chloro-perbenzoic acid, and additional inorganic salts such as potassium permanganate.

Suitable diluents for carrying out the third step of process (a) according to the invention are all solvents which are customary for such reactions. If hydrogen peroxide or peracids are used as oxidants, then acetic acid or glacial acetic acid is preferably employed as the diluent. If the process is carried out with potassium permanganate being used as the oxidant, then suitable solvents are preferably water or alcohols, such as tert-butanol.

When carrying out the third step of process (a) according to the invention, the reaction temperatures can be varied within a certain range. In general, the process is carried out at temperatures between 0° C. and 100° C., preferably between 10° C. and 100° C.

When carrying out the third step of process (a) according to the invention, an equivalent amount or an excess of oxidant is generally employed relative to 1 mol of compound of the formula (Ib). If it is desired to prepare SO compounds, then the process is generally carried out using, equimolar amounts. If it is intended to synthesize $SO_2$ compounds, an excess of oxidants will be selected. Working-up is carried out by customary methods. In general, a procedure is followed in which the mixture is diluted with ice or water, if appropriate rendered alkaline by adding a base, extracted using an organic solvent which is sparingly miscible with water, the combined organic phases are dried and concentrated and, if desired, the product which forms is recrystallized. If the process is carried out with potassium permanganate in aqueous solution, a procedure is generally followed in which the solid is filtered off, washed and dried.

Formula (IV) provides a general definition of the diaryl disulphides which are required as reactants for carrying out the first step of process (b) according to the invention.

$R^5$ preferably represents phenyl which can be monosubstituted to trisubstituted by identical or different substituents from the series consisting of halogen, alkyl having 1 to 4 carbon atoms and halogenoalkyl having 1 to 4 carbon atoms and 1 to 5 halogen atoms.

$R^5$ particularly preferably represents phenyl which can be monosubstituted to trisubstituted by identical or different substituents from the series consisting of fluorine, chlorine, bromine, methyl, ethyl, tert-butyl, trichloromethyl and/or trifluoromethyl.

$R^5$ very particularly preferably represents phenyl which can be monosubstituted or disubstituted by fluorine, chlorine, bromine, methyl, ethyl, tert-butyl, trichloromethyl and/or trifluoromethyl.

The diaryl disulphides of the formula (IV) are known or can be prepared by known methods.

Suitable strong bases for carrying out the first step of process (b) according to the invention are all those strong bases which have already been mentioned in connection with the description of the first step of process (a) according to the invention.

Diluents which are suitable for carrying out the first step of process (b) according to the invention are all those solvents which have already been mentioned in connection with the description of the first step of process (a) according to the invention.

The remaining reaction conditions and working-up methods for carrying out the first step of process (b) according to the invention, again, correspond to those which have already been mentioned in connection with the description of the first step of process (a) according to the invention.

Suitable oxidants for carrying out the second step of process (b) according to the invention are all those oxidants which have already been mentioned in connection with the description of the third step of process (a) according to the invention.

The reaction conditions and working,-up methods for carrying out the second step of process (b) according to the invention, again, are analogous to those which have already been mentioned in connection with the description of the third step of process (a) according to the invention. The same applies for the procedure of process (c) according to the invention.

The triazolyl derivatives of the formula (I) which can be obtained by the processes according to the invention can be converted to acid addition salts or metal salt complexes.

Suitable acids for the preparation of acid addition salts of the compounds of the formula (I) are preferably those which have already been mentioned in connection with the description of the acid addition salts according to the invention as being preferred acids.

Acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtering off, and, if appropriate, purified by washing with an inert organic solvent.

Suitable salts for the preparation of metal salt complexes of the compounds of the formula (I) are preferably those of metals which have already been mentioned in connection with the description of the metal salt complexes according to the invention as being preferred metal salts.

The metal salt complexes of the compounds of the formula (I) can be obtained in a simple manner by customary processes, for example by dissolving the metal salt in alcohol, for example ethanol, and adding the solution to compounds of the formula (I). Metal salt complexes can be isolated in a known manner, for example by filtering off, and, if appropriate, purified by recrystallization.

The active compounds according to the invention have a powerful microbicidal action and can be employed to control undesirable microorganisms, such as fungi and bacteria, in plant protection and materials protection.

Fungicides are employed in plant protection for combating Plasmodiophoromycetes, Oomycetes, Chytridiomycetes, Zygomycetes, Ascomycetes, Basidiomycetes, and Deuteromycetes.

Some causative organisms of fungal and bacterial diseases which come under the generic names listed above may be mentioned as examples, but not by way of limitation:

Xanthomonas species, such as *Xanthomonas oryzae;*
Pseudomonas species, such as *Pseudomonas lachrymans;*
Erwinia species, such as *Erwinia amylovora;*
Pythium species, such as *Pythium ultimum;*
Phytophthora species, such as *Phytophthora infestans;*
Pseudoperonospora species, such as *Pseudoperonospora humuli* or *Pseudoperonospora cubensis;*
Plasmopara species, such as *Plasmopara viticola;*
Peronospora species, such as *Peronospora pisi* or *P. brassicae;*
Erysiphe species, such as *Erysiphe graminis;*
Sphaerotheca species, such as *Sphaerotheca fuliginea;*
Podosphaera species, such as *Podosphaera leucotricha;*
Venturia species, such as *Venturia inaequalis;*
Pyrenophora species, such as *Pyrenophora teres* or *P. graminea*
(conidia form: Drechslera, syn: Helminthosporium);
Cochliobolus species, such as *Cochliobolus sativus,*
(conidia form: Drechslera, syn: Helminthosporium);
Uromyces species, such as *Uromyces appendiculatus;*
Puccinia species, such as *Puccinia recondita;*
Tilletia species, such as *Tilletia caries;*
Ustilago species, such as *Ustilago nuda* or *Ustilago avenae;*
Pellicularia species, such as *Pellicularia sasakii;*
Pyricularia species, such as *Pyricularia oryzae;*
Fusarium species, such as *Fusarium culmorum;*
Botrytis species, such as *Botrytis cinerea;*
Septoria species, such as *Septoria nodorum;*
Leptosphaeria species, such as *Leptosphaeria nodorum;*
Cercospora species, such as *Cercospora canescens;*
Alternaria species, such as *Alternaria brassicae* and
Pseudocercosporella species, such as *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds according to the invention are particularly suitable for combating *Pyricularia oryzae* and *Pellicularia sasakii* in rice and for combating cereal diseases, such as Pseudocercosporella, Erysiphe species and Fusarium species. Moreover, the substances according to the invention can be employed very successfully against Venturia and Sphaerotheca. In addition, they also have a very good in-vitro action.

In materials protection, the substances according to the invention can be employed for the protection of industrial materials from attack and destruction by undesirable microorganisms.

Industrial materials in the present connection are understood as meaning non-living materials which have been prepared for use in industry. For example, industrial materials which are to be protected from microbial change or destruction can be adhesives, glues, paper and cardboard, textiles, leather, wood, paints and plastic articles, cooling lubricants and other materials which can be attacked or decomposed by microorganisms. In the context of the materials to be protected, sections of production plants, for example cooling water circulations, may also be mentioned, which can be adversely affected by proliferation of microorganisms. In the context of the present invention, industrial materials which may preferably be mentioned are adhesives, glues, paper and cardboard, leather, wood, paints, cooling lubricants and heat-transfer fluids, particularly preferably wood.

Microorganisms which can cause breakdown or change of the industrial materials are, for example, bacteria, fungi, yeasts, algae and slime organisms. The active compounds according to the invention preferably act against fungi, in particular mould fungi, wood-discolouring and wood-destroying fungi (Basidiomycetes) and against slime organisms and algae.

For example, microorganisms of the following genera may be mentioned:
Alternaria, such as *Alternaria tenuis,*
Aspergillus, such as *Aspergillus niger,*
Chaetomium, such as *Chaetomium globosum,*
Coniophora, such as *Coniophora puetana,*
Lentinus, such as *Lentinus tigrinus,*
Penicillium, such as *Penicillium glaucum,*
Polyporus, such as *Polyporus versicolor,*
Aureobasidium, such as *Aureobasidium pullulans,*
Sclerophoma, such as *Sclerophoma pityophila,*
Trichoderma, such as *Trichoderma viride,*
Escherichia, such as *Escherichia coli,*
Pseudomonas, such as *Pseudomonas aeruginosa,*
Staphylococcus, such as *Staphylococcus aureus.*

Depending on their particular physical and/or chemical properties, the active compounds can be converted into the customary formulations, such as solutions, emulsions, suspensions, powders, foams, pastes, granules, aerosols, very fine capsules in polymeric substances and into coating compositions for seeds, as well as ULV cold and warn mist formulations.

These formulations are prepared in a known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general comprise between 0.1 and 95 per cent by weight of active compound, preferably between 0.5 and 90%.

When used in plant protection, the active compounds according to the invention can be used as such or, in their formulations, also as a mixture with known fungicides, bactericides, acaricides, nematicides or insecticides, for example so as to widen the spectrum of action or to prevent the build up of resistance. In many cases, this results in synergistic effects, i.e. the activity of the mixture exceeds the activity of the individual components.

Suitable components for the mixtures are, for example, the following substances:
Fungicides
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloro-N-(4-trifluoromethylbenzyl)benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino[alpha-(o-tolyloxy)-o-tolyl]acetate; 2-phenylphenol (OPP), aldimorph, ampropylfos, anilazine, azaconazole,
benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulfamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulfocarb, methfuroxam, metiram, metsulfovax, myclobutanil, nickel dimethyldithiocarbamate, nitrothal-isopropyl, nuarimol, ofurace, oxadixyl, oxamocarb, oxycarboxin, pefurazoate, penconazole, pencycuron, phosdiphen, pimaricin, piperalin, polyoxin, probenazole, prochloraz, procymidone, propamocarb, propiconazole, propineb, pyrazophos, pyrifenox, pyrimethanil, pyroquilon, quintozene (PCNB), sulphur and sulphur preparations, tebuconazole, tecloftalam, tecnazene, tetraconazole, thiabendazole, thicyofen, thiophanate-methyl, thiram, tolclophos-methyl, tolylfluanid, triadimefon, triadimenol, triazoxide, trichlamide, tricyclazole, tridemorph, triflumizole, triforine, triticonazole, validamycin A, vinclozolin, zineb, ziram.

Bactericides bronopol, dichlorophen, nitrapyrin, nickel dimethyldithiocarbamate, kasugamycin, octhilinone, furanecarboxylic acid, oxytetracyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin,

*Bacillus thuringiensis*, bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulfan, cartap, CGA 157 419, CGA 184699, chloethocarb, chlorethoxyfos chlorfenvinphos, chlorfluazuron, chliormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulfoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mervinphos, mesulfenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamdon, phoxim, pirimicarb, pirimiphos M, pirimiphos A, profenofos, promecarb, propaphos, propoxur, prothiofos, prothoate, pymetrozin, pyrachlophos, pyridaphenthion, pyresmethrin, pyrethrum, pyridaben, pyrimidifen, pyriproxifen, quinalphos, RH 5992, salithion, sebufos, silafluofen, sulfotep, sulprofos, tebufenozid, tebufenpyrad, tebupirimiphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, zetamethrin.

A mixture with other known active compounds, such as herbicides, or with fertilizers and growth regulators, is also possible.

The active compounds can be used as such or in the form of their formulations or the application forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the application forms can be varied within a relatively wide range: in general, they are between 1 and 0.0001% by weight, preferably between 0.5 and 0.001% by weight.

In the treatment of seed, in general amounts of active compound from 0.001 to 50 g per kilogram of seed are needed, preferably 0.01 to 10 g.

In the treatment of the soil, active compound concentrations of 0.00001 to 0.1% by weight are necessary at the site of action, preferably from 0.0001 to 0.02% by weight.

The compositions used for the protection of industrial materials in general contain the active compounds in an amount from 1 to 95%, preferably from 10 to 75%.

The application concentrations of the active compounds according to the invention depend on the nature and the occurrence of the microorganisms to be controlled and on the composition of the material to be protected. The optimum amount to be employed can be determined by a series of tests. In general, the application concentrations are in the range from 0.001 to 5% by weight, preferably from 0.05 to 1.0% by weight, based on the material to be protected.

The activity and the spectrum of action of the active compounds to be used in materials protection or the compositions, concentrates or, very generally, formulations which can be prepared therefrom can be increased if further antimicrobially active compounds, fungicides, bactericides, herbicides, insecticides or other active compounds are optionally added to increase the spectrum of action or achieve particular effects such as, for example, additional protection from insects. These mixtures can have a wider spectrum of action than the compounds according to the invention.

Preparation and use of the substances according to the invention can be seen from the examples which follow.

Preparation examples

EXAMPLE 1

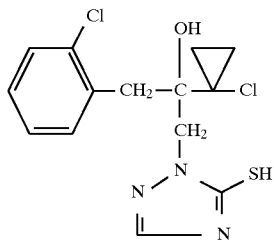 (I-1)

Variant α

A mixture of 3.12 g (10 mmol) of 2-(1-chloro-cyclopropyl)-1-(2-chlorophenyl)-3-(1,2,4-triazol-1-yl)-propan-2-ol and 45 ml of absolute tetrahydrofuran is treated at 20° C. with 8.4 ml (21 mmol) of n-butyl-lithium in hexane, and the mixture is stirred at 0° C. for 30 minutes. The reaction mixture is then cooled to −70° C., 0.32 g (10 mmol) of sulphur powder are added, and the mixture is stirred for 30 minutes at −70° C. It is heated to −10° C., and treated with ice-water and brought to a pH of 5 by adding dilute sulphuric acid. The mixture is extracted repeatedly using ethyl acetate, and the combined organic phases are dried over sodium sulphate and concentrated under reduced pressure. In this manner, 3.2 g (93% of theory) of 2-(1-chloro-cyclopropyl)-1-(2-chlorophenyl)-3-(5-mercapto-1,2,4-triazol-1-yl)-propan-2-ol are obtained in the form of a solid which, after recrystallization, melts at 138°–139° C.

Variant β

A mixture of 3.12 g (10 mmol) of 2-(1-chloro-cyclopropyl)-1-(2-chloro-phenyl)-3-(1,2,4-triazol-1-yl)-propan-2-ol, 0.96 g (30 mmol) of sulphur powder and 20 ml of absolute N-methyl-pyrrolidone is heated at 200° C. for 44 hours with stirring. The reaction mixture is then concentrated under reduced pressure (0.2 mbar). The crude product which is obtained (3.1 g) is recrystallized from toluene. In this manner, 0.7 g (20% of theory) of 2-(1-chloro-cyclopropyl)-1-(2-chlorophenyl)-3-(5-mercapto-1,2,4-triazol-1-yl)-propan-2-ol is obtained in the form of a solid substance of melting point 138°–139° C.

EXAMPLE 2

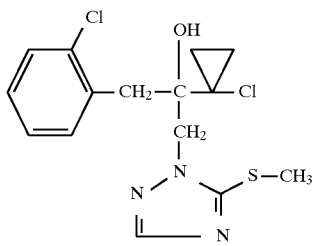 (I-2)

A mixture of 3.43 g (10 mmol) of 2-(1-chloro-cyclopropyl)-1-(2-chlorophenyl)-3-(5-mercapto-1,2,4-triazol-1-yl)-propan-2-ol, 20 ml of absolute acetonitrile and 1.38 g of (10 mmol) of potassium carbonate is treated with 0.93 ml (15 mmol) of methyl iodide and the mixture is stirred at 40° C. for 5 hours. The reaction mixture is then treated with saturated, aqueous sodium carbonate solution and extracted repeatedly using ethyl acetate. The combined organic phases are dried over sodium sulphate and concentrated under reduced pressure. In this manner, 3.4 g (95% of theory) of 2-(1-chloro-cyclopropyl)-1-(2-chlorophenyl)-3-(5-methylthio-1,2,4-triazol-1-yl)-propan-2-ol are obtained in the form of oil.

$^1$H NMR spectrum (200 MHz; CDCl$_3$, TMS): δ=0.6–1.05 (m, 4H); 2.7 (s, 3H); 3.35 (AB, 2H); 4.4 (AB, 2H); 4.7 (OH); 7.2–7.6 (m, 4H); 7.9 (s, 1H).

EXAMPLE 3

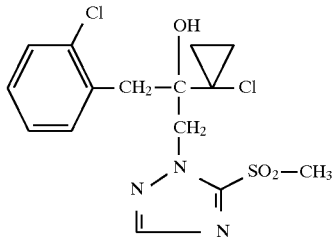 (I-2)

A solution of 3.57 g (10 mmol) of 2-(1-chlorocyclopropyl)-1-(2-chlorophenyl)-3-(5-methylthio-1,2,4-triazol-1-yl)-propan-2-ol in 40 ml of glacial acetic acid is treated dropwise at 90° C. with stirring with 4 ml of an aqueous hydrogen peroxide solution (35% strength). After the addition has ended, stirring of the reaction mixture is continued at 90° C. for 30 minutes, and the mixture is then cooled to room temperature, treated with ice and rendered alkaline by adding aqueous sodium hydroxide solution. The mixture is extracted repeatedly using ethyl acetate, and the combined organic phases are dried over sodium sulphate and concentrated under reduced pressure. The slowly crystallizing product which remains is filtered off with suction. In this manner, 2.0 g (51% of theory) of 2-(1-chloro-cyclopropyl)-1-(2-chlorophenyl)-3-(5-methylsulphonyl-1,2,4-triazol-1-yl)-propan-2-ol) are obtained in the form of a solid which melts at 125°–128° C.

EXAMPLE 4

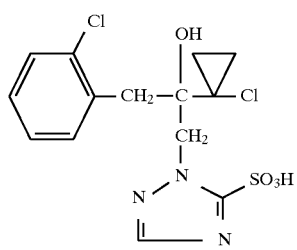
(I-4)

A mixture of 1.71 g (5 mmol) of 2-(1-chlorocyclopropyl)-1-(2-chlorophenyl)-3-(5-mercapto-1,2,4-triazol-1-yl)-propan-2-ol, 1.58 g (10 mmol) of potassium permanganate and 20 ml of water is stirred at room temperature for 30 minutes. The solid is then filtered off with suction, washed with water and dried. In this manner, 2.0 g (100% of theory) of 2-(1-chloro-cyclopropyl)-1-(2-chlorophenyl)-3-(5-sulpho-1,2,4-triazol-1-yl)-propan-2-ol are obtained in the form of a solid which melts at 68°–70° C.

EXAMPLE 5

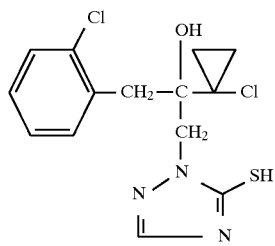
(I-5)

A mixture of 3.12 g (10 mmol) of 2-(1-chloro-cyclopropyl)-1-(2-chlorophenyl)-3-(1,2,4-triazol-1-yl)-propan-2-ol and 45 ml of absolute tetrahydrofuran is treated at −20° C. with 8.4 ml (21 mmol) of n-butyl-lithium in hexane and the mixture is stirred at 0° C. for 30 minutes. The reaction mixture is then cooled to −70° C., treated with 2.18 g (10 mmol) of diphenyl disulphide and slowly defrosted to room temperature, with stirring. Stirring is continued for another 19 hours at room temperature, and the mixture is diluted with ethyl acetate and repeatedly extracted by shaking with saturated aqueous sodium carbonate solution. The organic phase is dried over sodium sulphate and concentrated under reduced pressure. The 4.2 g of residue which remains is chromatographed over 500 g of silica gel using a mixture of petroleum ether/ethyl acetate =2:1. After the eluate has evaporated, 3.5 g (84% of theory) of 2-(1-chloro-cyclopropyl)-1-(2-chlorophenyl)-3-(5-phenylthio-1,2,4-triazol-1-yl)-propan-2-ol are obtained in the form of an oil.

Mass spectrum (CI): 420 (M+H$^+$)

EXAMPLE 6

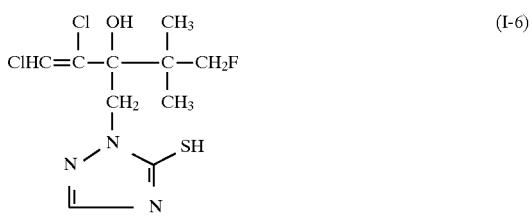
(I-6)

A mixture of 1.41 g (5 mmol) of 1,2-dichloro-4,4-dimethyl-5-fluoro-3-hydroxy-3-[(1,2,4-triazol-1-yl)-methyl]-1-pentene and 25 ml of absolute tetrahydrofuran is treated at −70° C. with 4 ml (10 mmol) of n-butyl-lithium in hexane and the mixture is stirred at −70° C. for one hour. The reaction mixture is then treated with 0.19 g (6 mmol) of sulphur powder and stirred at −70° C. for 4 hours. It is then hydrolysed by adding 1 ml of methanol and 1 ml of acetic acid at −70° C. The reaction mixture is first diluted with ethyl acetate and then extracted by shaking several times with saturated, aqueous ammonium chloride solution. The organic phase is dried over sodium sulphate and concentrated under reduced pressure. The crude product (1.7 g) which is obtained is purified by chromatography on silica gel using a mixture of petroleum ether and ethyl acetate =1:1 as eluent. In this way, 0.5 g (32% of theory) of 1,2-dichloro-4,4-dimethyl-5-fluoro-3-hydroxy-3-[(5-mercapto- 1,2,4-triazol-1-yl)-methyl]-1-pentene is obtained in the form of a solid substance of melting point 162°–164° C.

The substances shown in the following Table 2 are also prepared according to the methods indicated previously.

TABLE 2

(Ia)

| Ex. No. | Compound No. | R$^1$ | R$^2$ | Physical constant |
|---|---|---|---|---|
| 7 | (I-7) | —CCl=CHCl | —C(CH$_3$)$_3$ | M.p. 168–169° C. |
| 8 | (I-8) | OCHF$_2$-phenyl | cyclopropyl-Cl | GC/MS (CI): 376 (M + H$^+$) |

TABLE 2-continued
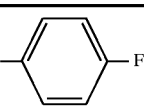
(Ia)
| Ex. No. | Compound No. | R¹ | R² | Physical constant |
|---|---|---|---|---|
| 9 | (I-9) |  | 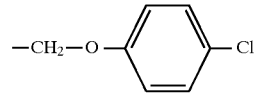 | M.p. 163–164° C. |
| 10 | (I-10) | 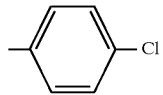 | —C(CH₃)₃ | M.p. 127° C. |
| 11 | (I-11) | 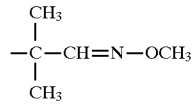 | 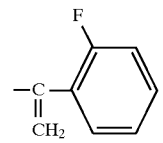 | Oil |
| 12 | (I-12) |  | 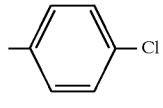 | GC/MS (Cl): 340 (M + H⁺) |
| 13 | (I-13) | 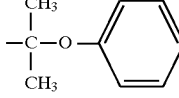 | 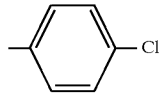 | GC/MS (Cl): 424 (M + H⁺) |
| 14 | (I-14) |  |  | M.p. 168° C. |
| 15 | (I-15) |  | 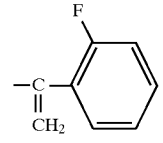 | GC/MS (Cl): 314 (M + H⁺) |
| 16 | (I-16) | 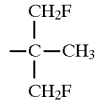 | 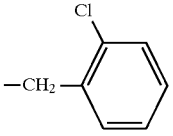 | GC/MS (Cl): 346 (M + H⁺) |
| 17 | (I-17) |  | 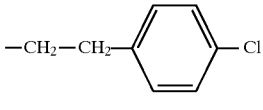 | M.p. 115–118° C. |
| 18 | (I-18) | 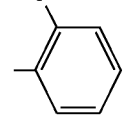 | —C(CH₃)₃ | GC/MS (Cl): 340 (M + H⁺) |
| 19 | (I-19) | 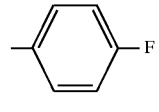 | | GC/MS (Cl): 334 (M + H⁺) |

TABLE 2-continued (Ia)

R¹—C(OH)(R²)—CH₂—N(N=... pyrazole-SH ring)

| Ex. No. | Compound No. | R¹ | R² | Physical constant |
|---|---|---|---|---|
| 20 | (I-20) | 2,4-dichlorophenyl | —C₄H₉-n | *) |

*) The compound is characterized by the following signals in the $^1H$—NMR spectrum (400 MHz, $CDCl_3$/TMS):
δ = 0.8(t, 3H); 0.85(m, 2H); 1.25(m, 2H); 1.8(m, 1H); 2.55(m, 1H); 4.6(OH); 4.9(AB, 2H); 7.2(dd, 1H); 7.35(d, 1H); 7.7(s, 1H); 7.75(d, 1H); 12.3(5H)ppm

Use Examples

Example A

Erysiphe test (barley)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the plants are dusted with spores of Erysiphe graminis f.sp.hordei.

The plants are placed in a greenhouse at a temperature of about 20° C. and a relative atmospheric humidity of about 80%, in order to promote the development of mildew pustules.

Evaluation is carried out 7 days after the inoculation.

The active compounds, active compound concentrations and test results are shown in the following table.

TABLE A

Erysiphe test (barley)/protective

| Active compound | Degree of effectiveness in % of the untreated control at an active compound application rate of 250 g/ha |
|---|---|
| According to the invention: | 100 |
| (1) 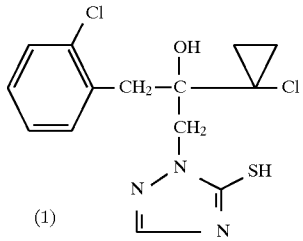 | |

Example B

Erysiphe test (wheat)/protective

Solvent: 10 parts by weight of N-methyl-pyrrolidone

Emulsifier: 10 parts by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the plants are dusted with spores of Erysiphe graminis f.sp. tritici.

The plants are placed in a greenhouse at a temperature of about 20° C. and a relative atmospheric humidity of about 80%, in order to promote the development of mildew pustules.

Evaluation is carried out 7 days after the inoculation.

The active compounds, active compound concentrations and test results are shown in the following table.

TABLE B

Erysiphe test (wheat)/protective

| Active compound | Degree of effectiveness in % of the untreated control at an active compound application rate of 250 g/ha |
|---|---|
| According to the invention: | 100 |
| (1) 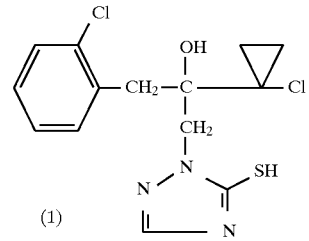 | |

Example C
Pseudocercosporella herpotrichoides test (wheat)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the stem base of the plants is inoculated with spores of Pseudocercosporella herpotrichoides.

The plants are placed in a greenhouse at a temperature of about 10° C. and a relative atmospheric humidity of about 80%.

Evaluation is carried out 21 days after the inoculation.

The active compounds, active compound concentrations and test results are shown in the following table.

TABLE C

Pseudocercosporella herpotrichoides test (wheat)/protective

| Active compound | Degree of effectiveness in % of the untreated control at an active compound application rate of 250 g/ha |
|---|---|
| According to the invention: (1) | 100 |
| Disclosed in EP-A 0 297 345: | 75 |

Example D
Fusarium nivale (var. nivale) test (wheat)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the plants are sprayed with a conidia suspension of Fusarium nivale var. nivale.

The plants are placed in a greenhouse under transparent incubation cages at a temperature of about 15° C. and a relative atmospheric humidity of about 100%.

The active compounds, active compound concentrations and test results are shown in the following table.

TABLE D

Fusarium nivale (var. nivale) test (wheat)/protective

| Active compound | Degree of effectiveness in % of the untreated control at an active compound application rate of 250 g/ha |
|---|---|
| According to the invention: (1) | 100 |

Example E
Fusarium culmorum test (wheat)/protective

Solvent: 10 parts by weight of N-methyl-pyrrolidone

Emulsifier: 0.6 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound at the application rate shown. After the spray coating has dried on, the plants are sprayed with a conidia suspension of Fusarium culmorum.

The plants are placed in a greenhouse under transparent incubation cages at a temperature of about 20° C. and a relative atmospheric humidity of about 100%.

Evaluation is carried out 4 days after the inoculation.

The active compounds, active compound concentrations and test results are shown in the following tables.

TABLE E-1

Fusarium culmorum test (wheat)/protective

| Active compound | Degree of effectiveness in % of the untreated control at an active compound application rate of 250 g/ha |
|---|---|
| According to the invention: (1) | 100 |

TABLE E-2

Fusarium culmorum test (wheat)/protective

| Active compound | Degree of effectiveness in % of the untreated control at an active compound application rate of 25 g/ha |
|---|---|
| Disclosed in EP-A 0 461 502: | 50 |
| According to the invention: (16) | 75 |

TABLE E-3

Fusarium culmorum test (wheat)/protective

| Active compound | Degree of effectiveness in % of the untreated control at an active compound application rate of 125 g/ha |
|---|---|
| Disclosed in EP-A 564 810: | 88 |
| According to the invention: (17) | 100 |

Example F

Pellicularia-Test (rice)

Solvent: 12.5 parts by weight of acetone

Emulsifier: 0.3 part by weight of alkylaryl polyglycol ether

To produce a suitable preparation of active compound, 1 part by weight of active compound is mixed with the stated amount of solvent, and the concentrate is diluted with water and the stated amount of emulsifier to the desired concentration.

To test for activity, young rice plants in the 3 to 4 leaf stage are sprayed until dripping wet. The plants remain in a greenhouse until they have dried. The plants are then inoculated with *Pellicularia sasakii* and are placed at 25° C. and 100% relative atmospheric humidity.

The evaluation of the disease infestation is carried out 5 to 8 days after the inoculation.

The active compounds, active compound concentrations and test results are shown in the following table.

TABLE F

Pellicularia test (rice)

| Active compound | Active compound concentration in the spray mixture in % by weight | Degree of effectiveness in % of the untreated control |
|---|---|---|
| According to the invention: (1) | 0.025 | 100 |

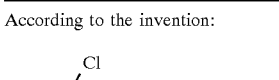

Example G

Sphaerotheca test (cucumber)/protective

Solvent: 4.7 parts by weight of acetone

Emulsifier: 0.3 part by weight of alkylaryl polyglycol ether

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

The active compounds, active compound concentrations and test results are shown in the following table.

TABLE G

Sphaerotheca test (cucumber)/protective

| Active compound | Degree of effectiveness in % of the untreated control at an active compound application rate of 1 ppm |
|---|---|
| According to the invention: | 100 |

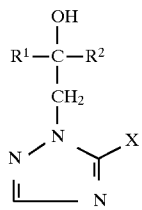
(1)

We claim:
1. A triazolyl derivative of the formula

$$\begin{array}{c} \text{OH} \\ | \\ R^1 - C - R^2 \\ | \\ CH_2 \\ | \\ N \diagdown N \diagup X \\ \| \\ N \end{array} \quad (I)$$

in which
R¹ represents straight-chain or branched alkenyl having 2 to 5 carbon atoms, wherein each of these radicals is optionally monosubstituted to trisubstituted by identical or different substituents selected from the group consisting of chlorine, bromine, methoxy, ethoxy, propoxy, isopropoxy, cyclopropyl, cyclobutyl, cyclopentyl and cyclohexyl,
and
R² represents n-propyl, isopropyl, n-butyl, i-butyl, sec-butyl or tert-butyl, wherein each of these radicals is optionally monosubstituted to tetrasubstituted by identical or different substituents selected from the group consisting of fluorine, bromine, methoxy, ethoxy, propoxy, isopropoxy, methoximino, ethoximino, cyclopropyl, cyclobutyl, cyclopentyl and cyclohexyl,
or
represents straight-chain or branched alkenyl having 2 to 5 carbon atoms, wherein each of these radicals is optionally monosubstituted to trisubstituted by identical or different substituents selected from the group consisting of fluorine, chlorine, bromine, methoxy, ethoxy, propoxy, isopropoxy, cyclopropyl, cyclobutyl, cyclopentyl and cyclohexyl,
or
represents 1-methyl-cyclohexyl, cyclohexyl, 1-chlorocyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl,
or
represents phenylalkyl having 1 or 2 carbon atoms in the straight-chain or branched alkyl moiety, wherein the phenyl moiety is optionally monosubstituted to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano,
or
represents phenylalkenyl having 2 to 4 carbon atoms in the alkenyl moiety, wherein the phenyl moiety is optionally monosubstituted to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximino-methyl, 1-methoximinoethyl, nitro and cyano,
or
represents phenoxyalkyl having 1 to 4 carbon atoms in the straight-chain or branched oxyalkyl moiety, wherein the phenyl moiety is optionally monosubstituted to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano,
or
represents phenyl which is optionally monosubstituted to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethoxy, chlorodifluoromethylthio, methoxycarbonyl, ethoxycarbonyl, methoximinomethyl, 1-methoximinoethyl, nitro and cyano,
or
R¹ represents phenylalkenyl having 2 to 4 carbon atoms in the alkenyl moiety, wherein the phenyl moiety is optionally monosubstituted to trisubstituted by identical or different substituents selected from the group consisting of fluorine, chlorine, bromine, methyl, ethyl, tert-butyl, methoxy, ethoxy, methylthio, trifluoromethyl, trifluoromethoxy, trifluoromethylthio, chlorodifluoromethoxy, difluoromethyl, chlorodifluoromethylthio, methoxycarbonyl, ethoxycarbonyl, methoximinomethyl, 1-methoximinoethyl, nitro and cyano,
and
R² represents 1-methyl-cyclohexyl, cyclohexyl, 1-chloro-cyclopropyl, 1-fluoro-cyclopropyl, 1-methyl-cyclopropyl, 1-cyano-cyclopropyl, cyclopropyl, 1-methyl-cyclopentyl or 1-ethyl-cyclopentyl,
and
X represents the groups —SH, —SR³, —SO—R³, —SO₂—R³ or —SO₃H₁ in which
R³ represents methyl, ethyl or propyl, wherein each of these radicals is optionally monosubstituted to trisubstituted by identical or different substituents selected from the series consisting of fluorine and chlorine, or
 represents allyl, but-2-en-yl or but-3-enyl, wherein each of these radicals is optionally monosubstituted or trisubstituted by identical or different substituents selected from the group consisting of fluorine and chlorine,
or
 represents phenylalkyl having 1 to 2 carbon atoms in the straight-chain or branched alkyl moiety, wherein each of these radicals is optionally monosubstituted or disubstituted in the phenyl moiety by fluorine, chlorine, bromine, methyl, ethyl, tert-butyl, trichloromethyl and trifluoromethyl,
or
 represents phenyl which is optionally monosubstituted or disubstituted by fluorine, chlorine, bromine, methyl, ethyl, tert-butyl, trichloromethyl and trifluoromethyl,
or an addition product thereof with an acid or metal salt.

2. A microbicidal composition comprising a microbicidally effective amount of a compound or addition product as claimed in claim 1 and an inert diluent.

3. A method of controlling undesired microorganisms in plant protection and in the preservation of materials, which method comprises applying to such undesired microorganisms or to their habitat a microbicidally effective amount of a compound or addition product as claimed in claim 1.

4. A triazolyl derivative of the formula (I) according to claim 1, which is 1,2-dichloro-4,4-dimethyl-5-fluoro-3-hydroxy-3-[(5-mercapto-1,2,4-triazol-1-yl) -methyl]-1-pentene of the formula:

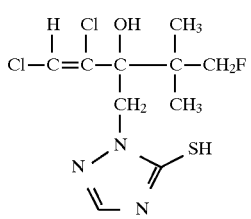

* * * * *